United States Patent [19]

Neumann et al.

[11] Patent Number: 4,476,135

[45] Date of Patent: Oct. 9, 1984

[54] AMINO-2,1,3-BENZOTHIADIAZOLE AND -BENZOXADIAZOLE DERIVATIVES, THEIR PREPARATION AND PHARMACEUTICAL COMPOSITIONS CONTAINING THEM

[75] Inventors: Peter Neumann, Berne; Gerhard Bormann, Münchenstein, both of Switzerland

[73] Assignee: Sandoz Ltd., Basel, Switzerland

[21] Appl. No.: 348,872

[22] Filed: Feb. 16, 1982

[30] Foreign Application Priority Data

Feb. 19, 1981 [CH] Switzerland .................. 1110/81
Feb. 19, 1981 [CH] Switzerland .................. 1111/81
Oct. 9, 1981 [CH] Switzerland .................. 6480/81

[51] Int. Cl.$^3$ .................. A61K 31/425; A61K 31/42; C07D 233/28
[52] U.S. Cl. .................. 424/270; 424/272; 544/331; 548/126; 548/351
[58] Field of Search .................. 548/126, 351; 544/331; 424/270, 272

[56] References Cited

U.S. PATENT DOCUMENTS

| | | | |
|---|---|---|---|
| 3,636,219 | 1/1972 | Culik et al. | 425/265 |
| 3,708,485 | 1/1973 | Stähle et al. | 260/254 |
| 3,843,668 | 10/1974 | Neumann | 548/126 |
| 4,217,356 | 8/1980 | Neumann | 548/126 |
| 4,277,487 | 7/1981 | Stähle et al. | 548/351 |
| 4,327,106 | 4/1982 | Stähle et al. | 548/351 |
| 4,333,945 | 6/1982 | Ringwald | 424/270 |
| 4,361,575 | 11/1982 | Stähle et al. | 548/351 |

FOREIGN PATENT DOCUMENTS 579565 3/1973 Switzerland .................. 548/126
625238 12/1976 Switzerland .................. 548/126

OTHER PUBLICATIONS

Burger, Medicinal Chemistry, IInd Ed. (1960), p. 42, Interscience Publishers, Inc. N.Y.

Primary Examiner—Donald G. Daus
Assistant Examiner—Cecilia Shen
Attorney, Agent, or Firm—Gerald D. Sharkin; Robert S. Honor; Joseph J. Borovian

[57] ABSTRACT

The compounds of formula I $$\begin{array}{c} A \\ | \\ B \\ | \\ C \end{array} \qquad I$$

wherein
A is an optionally substituted 2,1,3-benzothiadiazole or 2,1,3-benzoxadiazole moiety,
B is a trisubstituted amino group and
C is an optionally 1-substituted 4,5-dihydro-1H-imidazol-2-yl or an optionally 3-substituted 3,4,5,6-tetrahydropyrimidin-2-yl moiety.

are useful as bradycardiac agents, as anti-tremor, anti-rigor and myotonolytic agents, as tranquillizers and as antidepressants.

6 Claims, No Drawings

AMINO-2,1,3-BENZOTHIADIAZOLE AND -BENZOXADIAZOLE DERIVATIVES, THEIR PREPARATION AND PHARMACEUTICAL COMPOSITIONS CONTAINING THEM

The present invention relates to amino-2,1,3-benzothiadiazole and -benzoxadiazole derivatives, their preparation and pharmaceutical compositions containing them.

In particular, the invention provides compounds of formula I

wherein

A is an optionally substituted 2,1,3-benzothiadiazole or 2,1,3-benzoxadiazole moiety, B is a trisubstituted amino group and C is an optionally 1-substituted 4,5-dihydro-1H-imidazol-2-yl or an optionally 3-substituted 3,4,5,6-tetrahydropyrimidin-2-yl moiety, hereinafter referred to as "the compounds of the invention".

In accordance with the invention, there are especially provided compounds of formula Ia,

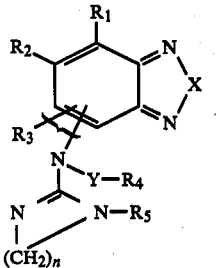

wherein n is 2 or 3,

X is oxygen or sulfur,

Y is a bond or oxygen, $R_1$, $R_2$ and $R_3$ independently are hydrogen, halogen of atomic number of from 9 to 53, cyano, hydroxy, alkyl of 1 to 4 carbon atoms, alkoxy of 1 to 4 carbon atoms or alkylthio of 1 to 4 carbon atoms, $R_4$ is (i) alkyl of 1 to 6 carbon atoms optionally monosubstituted by hydroxy or halogen of atomic number of from 9 to 53 and wherein the hydroxy or halogen moiety is separated from Y by at least 2 carbon atoms; alkenyl of 3 to 6 carbon atoms optionally monosubstituted by halogen of atomic number of from 9 to 53 and wherein the double bond and the halogen moiety are separated from Y by at least 2 carbon atoms; alkinyl of 3 to 6 carbon atoms wherein the triple bond is separated from Y by at least 2 carbon atoms; cycloalkyl of 3 to 7 carbon atoms; cycloalkylalkyl of 3 to 7 carbon atoms in the cycloalkyl moiety and of 1 to 4 carbon atoms in the alkyl moiety thereof;

(ii) 2,2,5,5-tetraalkylpyrrolidin-1-ylalkyl or 2,2,6,6-tetraalkylpiperidin-1-ylalkyl independently of 1 to 4 carbon atoms in each of the alkyl moieties of the pyrrolidine or piperidine moiety, of 2 to 5 carbon atoms in the alkyl moiety bound to Y and wherein the nitrogen atom of the pyrrolidine or piperidine moiety is separated from Y by at least 2 carbon atoms; furanylalkyl, thienylalkyl or pyridylalkyl each of 1 to 4 carbon atoms in the alkyl moiety thereof; or morpholin-1-ylalkyl of 2 to 5 carbon atoms in the alkyl moiety thereof and wherein the nitrogen atom of the morpholine moiety is separated from Y by at least 2 carbon atoms;

(iii) phenylalkyl of 7 to 11 carbon atoms, phenoxyalkyl of 8 to 12 carbon atoms wherein the oxygen atom is separated from Y by at least 2 carbon atoms, phenylcarbonylalkyl of 8 to 12 carbon atoms, phenylalkoxyalkyl of 1 to 4 carbon atoms in the alkoxy and of 2 to 5 carbon atoms in the alkyl moiety thereof and wherein the oxygen atom is separated from Y by at least 2 carbon atoms, phenylalkenyl of 9 to 13 carbon atoms wherein the double bond is separated from Y by at least 2 carbon atoms, phenylalkinyl of 9 to 13 carbon atoms wherein the triple bond is separated from Y by at least 2 carbon atoms, all the phenyl rings in the six above-mentioned substituents optionally being mono- or independently di-substituted by alkyl of 1 to 4 carbon atoms, alkoxy of 1 to 4 carbon atoms or halogen of atomic number of from 9 to 53 or, when Y is a bond, alternatively or additionally also by hydroxy; or (iv) when Y is oxygen, additionally hydrogen, and $R_5$ is hydrogen or alkyl of 1 to 4 carbon atoms.

It is to be appreciated that the compounds of the invention are defined with reference to one specific tautomeric form, e.g. that of formula Ia, only for the sake of simplicity. However, the invention extends to all tautomeric forms of the compounds of formula Ia.

It is also to be appreciated that any carbon chain of more than 2 carbon atoms may be branched or straight-chained.

Alkyl of 1 to 4 carbon atoms or of 1 to 6 carbon atoms and/or alkoxy and/or alkylthio preferably are of 1 or 2, especially of 1 carbon atom. Halogen preferably is chlorine or bromine, especially chlorine. When alkyl of 1 to 6 carbon atoms is substituted by hydroxy, it is especially substituted in the ω-position. Alkenyl is preferably of 3 or 4 carbon atoms, it especially is allyl. When it is substituted by halogen, it preferably is substituted at a carbon atom bound to the double bond; it is then especially 2-chloro-2-propenyl. Alkinyl preferably is of 3 or 4 carbon atoms; it especially is 2-propinyl. Cycloalkyl preferably is of 3,5 or 6 carbon atoms; it especially is cyclopentyl. Cycloalkylalkyl preferably is of 3, 5 or 6, especially of 3 carbon atoms in the cycloalkyl moiety thereof and preferably of 1 or 2, especially of 1 carbon atom in the alkyl moiety thereof. In 2,2,5,5-tetraalkylpyrrolidin-1-ylalkyl and 2,2,6,6-tetraalkylpiperidin-1-ylalkyl the alkyl substituents preferably are methyl or ethyl, especially methyl; they preferably are identical; the bridging alkylene moiety preferably is ethylene. Furanylalkyl preferably is furanylmethyl, especially 2-furanylmethyl. Thienylalkyl preferably is thienylmethyl, especially 2-thienylmethyl. Pyridylalkyl preferably is pyridylmethyl, especially 2- or 3-, especially 2-pyridylmethyl. Morpholin-1-ylalkyl preferably is morpholin-1-ylethyl. Phenylalkyl preferably is benzyl or phenylethyl, optionally substituted. Phenoxyalkyl preferably is phenoxyethyl, optionally substituted. Phenylalkoxyalkyl preferably is benzyloxyethyl, optionally substituted. Phenylalkenyl preferably is cinnamyl, optionally substituted. Phenylalkinyl preferably is 3-phenyl-2-propinyl, optionally substituted.

When a phenyl ring as part of a substituent R₄ is substituted, it preferably is substituted in the para position. When it is disubstituted, it preferably is substituted in the meta and para positions. The substituents preferably are identical. Preferred as substituents are halogen, alkyl and alkoxy, especially alkoxy.

n preferably is 2. X preferably is sulfur. Y preferably is a bond. $R_1$ and/or $R_2$ preferably are hydrogen, halogen, alkyl, alkoxy or cyano, especially hydrogen. They preferably are identical when they both are other than hydrogen. $R_3$ preferably is hydrogen, hydroxy, alkyl, alkoxy or halogen, especially hydrogen. The nitrogen atom carrying Y—R₄ preferably is bound at the 4 position of the 2,1,3-benzothiadiazole or 2,1,3-benzoxadiazole ring. R₄ preferably has the above-defined significance (i) or (iii), especially significance (i). R₅ preferably is hydrogen. Significance (i) preferably is alkyl optionally substituted by hydroxy, especially alkyl, or is alkenyl or cycloalkylalkyl, it especially is alkenyl. The above-defined significance (ii) preferably is morpholinylalkyl. Significance (iii) preferably is optionally substituted phenylalkyl, phenoxyalkyl, phenylalkoxyalkyl or phenylalkenyl.

One group of compounds of the invention is the compounds of formula Ipa

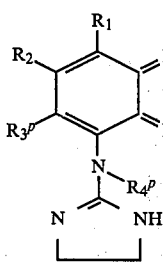

Ipa wherein $R_1$ and $R_2$ are as defined above, $R_3^p$ has the significance indicated above for $R_3$ and $R_4^p$ is (i) alkyl of 1 to 6 carbon atoms; alkenyl of 3 to 6 carbon atoms wherein the double bond is separated from the nitrogen atom by at least 2 carbon atoms; 2-chloro-2-propenyl; alkinyl of 3 to 6 carbon atoms wherein the triple bond is separated from the nitrogen atom by at least 2 carbon atoms; cycloalkyl of 3 to 7 carbon atoms; cycloalkylalkyl of 3 to 6 carbon atoms in the cycloalkyl moiety and of 1 to 4 carbon atoms in the alkyl moiety thereof, the total number of carbon atoms not exceeding 7;

(ii) thienylmethyl, 2-furanylmethyl or pyridylmethyl; or (iii) benzyl or cinnamyl.

A further group of compounds of the invention is the compounds of formula Ipb

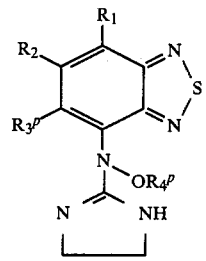

Ipb wherein $R_1$, $R_2$, $R_3^p$ and $R_4^p$ are as defined above.

A compound of the invention may be obtained by a process comprising (a) appropriately substituting a corresponding compound of formula II

II wherein A and C are as defined above and B' is a secondary amino group or (b) reacting a corresponding compound of formula III

III wherein A and B are as defined above and Q is a group capable of cyclization with a diamine, with a corresponding, optionally 1-substituted ethylene or propylene diamine.

In particular, a compound of formula Ia may be obtained by (a) appropriately substituting the bridging nitrogen atom in a corresponding compound of formula IIa

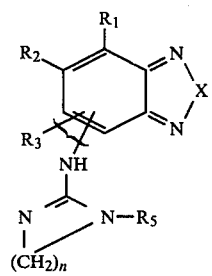

IIa wherein n, X, $R_1$, $R_2$, $R_3$ and $R_5$ are as defined above or (b) for the production of a compound of formula Iaa,

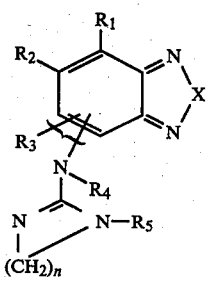

wherein n, X and $R_1$ to $R_5$ are as defined above, reacting a corresponding compound of formula IIIa

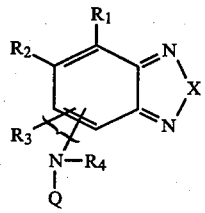

wherein Q, X and $R_1$ to $R_4$ are as defined above, with a corresponding compound of formula IV

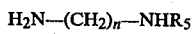

$$H_2N\text{---}(CH_2)_n\text{---}NHR_5 \qquad IV$$

wherein n and $R_5$ are as defined above.

Process variant (a) may be effected in conventional manner for the production of analogous trisubstituted amines by substitution of a secondary amine.

For the production of a compound wherein the substituent to be introduced is to be bound to the nitrogen atom over a carbon atom, the reaction conditions of an N-alkylation of a secondary amine may be used.

An appropriate N-alkylating agent is e.g. a compound of formula Z—$R_4$ wherein $R_4$ is as defined above and Z is a leaving group, e.g. halogen or a group $R_z$—$SO_2$—O—, wherein $R_z$ is phenyl, tolyl or lower alkyl. Z especially is bromine or chlorine. The reaction is conveniently effected in an organic solvent such as dimethylformamide or an alcohol. Preferably a basic condensation agent such as sodium carbonate, pyridine or N-ethyl-N,N-diisopropylamine is used. The reaction temperature may vary between room temperature and approximately 100° C.

For the production of a compound wherein the substituent to be introduced is to be bound to the nitrogen atom over an oxygen atom, the reaction preferably is effected in two stages, e.g. as follows:

In a first stage, a compound of formula II is substituted at the secondary amino group with hydroxy. To this effect a compound of formula II is oxidized with an oxidizing agent such as 3-chloroperbenzoic acid. Conveniently an inert solvent such as methylene chloride is used. The reaction preferably is effected at a temperature from about 0° to about 25° C. A corresponding compound substituted at the nitrogen atom by hydroxy is obtained.

In a second stage, if required, the resultant hydroxy compound is then O-alkylated. Conveniently, reaction conditions similar to those indicated above for N-alkylation may be used. Preferably strongly alkaline conditions, as e.g. in the presence of sodium ethylate, are used.

The reactivities of any substituents present should be taken into account. Thus, when the 2,1,3-benzothiadiazole or 2,1,3-benzoxadiazole ring is substituted e.g. by hydroxy, it may be indicated to effect the above-mentioned oxidation and O-alkylation with the phenolic hydroxy group or groups in protected form, and to deprotect thereafter. Methyl is an example of a phenolic hydroxy protecting group. It may be split off e.g. with trimethylsilyl iodide or the lithium salt of ethyl mercaptan. When $R_4$ is phenylcarbonylalkyl the carbonyl moiety may also be temporarily protected e.g. in the form of a 1,3-dioxolane ring.

Process variant (b) may also be effected in conventional manner for the production of analogous 2-amino-4,5-dihydro-1H-imidazoles or 2-amino-3,4,5,6-tetrahydropyrimidines.

Q is e.g. cyano, —C($NH_2$)=NH, —C(SAlk)=NH or —C(OAlk)=NH wherein Alk is lower alkyl, preferably methyl, or is e.g. —COOAlk', wherein Alk' is lower alkyl, preferably ethyl. Q especially is cyano.

The reaction preferably is effected in an inert organic solvent, e.g. an alcohol of 3 to 8 carbon atoms such as n-pentanol or a hydrocarbon such as xylol. The reaction preferably is effected in the presence of an excess of a monovalent salt of the ethylene or propylene diamine. When a large excess of the diamine in free base form is used, then it may also serve as a solvent. The reaction temperature is about 50° to about 200° C., preferably about 110° to about 150° C.

The compounds of the invention may be isolated from the reaction mixture and purified in a manner analogous to known methods.

The compounds of the invention may exist in free form, normally as a base, or in salt form. Free forms may be converted into salt forms in conventional manner and vice-versa. Suitable acids for acid addition salt formation include hydrochloric, malonic, p-toluene-sulfonic and methanesulfonic acid. Suitable bases for anionic salt formation, e.g. when $R_1$, $R_2$ and/or $R_3$ is hydroxy, include sodium and potassium hydroxide.

The starting material may be obtained in known manner.

A compound of formula IIIa wherein Q is cyano may e.g. be obtained by appropriately substituting the bridging nitrogen atom in a corresponding N-cyano-2,1,3-benzothiadiazol- or N-cyano-2,1,3-benzoxadiazol-4-amine.

Insofar as the preparation of any particular starting material is not particularly described, this may be effected in conventional manner or in analogous manner to that described herein.

In the following Examples all temperatures are in degrees Centigrade and are uncorrected.

EXAMPLE 1

N-allyl-5-chloro-N-(4,5-dihydro-1H-imidazol-2-yl)-2,1,3-benzothiadiazol-4-amine (process variant a)

38 g Allyl bromide are added to a solution of 20 g 5-chloro-N-(4,5-dihydro-1H-imidazol-2-yl)-2,1,3-benzothiadiazol-4-amine in 500 ml methanol, 20 ml dimethylformamide and 9 ml pyridine. The mixture is stirred and heated for 19 hours under reflux, and then the pale yellow solution evaporated under reduced pressure. The residue is stirred in water and the resulting crystalline hydrobromide of the title compound filtered and washed with cold water. The salt is made alkaline with 20% sodium hydroxide, and the free base extracted with methylene chloride. The organic phase is dried with sodium sulfate and the solvent evaporated. The residue is recrystallized from ethyl acetate. The title compound is obtained (M.P. of the free base form 140°–142°; M.P. of the hydrochloride salt form 218°–219°).

EXAMPLE 2

5-chloro-N-hydroxy-N-(4,5-dihydro-1H-imidazol-2-yl)-2,1,3-benzothiadiazol-4-amine (process variant a)

To a stirred suspension of 7.5 g 5-chloro-N-(4,5-dihydro-1H-imidazol-2-yl)-2,1,3-benzothiadiazol-4-amine in 600 ml of methylene chloride are added at 5° over 20 minutes 7.5 g of m-chloroperbenzoic acid. The solution is stirred for 100 minutes at room temperature and then extracted successively with 60 ml and twice 30 ml of 2N sodium hydroxide. The combined extracts are then acidified with 1N aqueous hydrochloric acid solution. The precipitated m-chlorobenzoic acid is filtered off, the solvent evaporated to dryness, the residue dissolved in 500 ml ethanol, the precipitated sodium chloride filtered off, the filtrate treated with charcoal and the solvent evaporated to dryness. The residue is recrystallized from isopropanol. The title compound is obtained (M.P. of the hydrochloride salt form 220°–222° [dec.]).

EXAMPLE 3

5-chloro-N-(4,5-dihydro-1H-imidazol-2-yl)-N-(2-phenoxyethoxy)-2,1,3-benzothiadiazol-4-amine (process variant a)

5 g 5-chloro-N-hydroxy-N(4,5-dihydro-1H-imidazol-2-yl-2,1,3-benzothiadiazol-4-amine hydrochloride (obtained according to Example 2 above) are added to a solution of 0.68 g sodium in 70 ml ethanol followed by 3.77 g 2-bromoethyl phenyl ether. The mixture is stirred for 2 hours at room temperature. The resulting precipitate is filtered off and the filtrate evaporated under reduced pressure. The residue is dissolved in methylene chloride and washed with 1N hydrochloric acid. The organic phase is dried with sodium sulfate and the solvent evaporated. The title compound is obtained (M.P. of the hydrochloride salt form 161°–162°).

EXAMPLE 4

N-allyl-5-chloro-N-(4,5-dihydro-1H-imidazol-2-yl)-2,1,3-benzothiadiazol-4-amine (process variant b)

9.5 g toluene sulfonic acid monohydrate and 3 g ethylene diamine are dissolved in 3 ml water and reacted with a solution of 2.5 g N-allyl-5-chloro-N-cyano-2,1,3-benzothiadiazol-4-amine in 10 ml xylol. The mixture is heated 4 hours under refluxing; after cooling 100 ml of 2N hydrochloric acid solution are added and the mixture is extracted twice with 60 ml methylene chloride. The aqueous phase is treated with charcoal, made alkaline with concentrated aqueous ammonia solution and then extracted with methylene chloride. The organic phase is dried and the solvent evaporated. The residue is recrystallized from ethyl acetate. The title compound is obtained (M.P. of the free base form 140°–142°; M.P. of the hydrochloride salt form 218°–219°).

The starting material is obtained as follows: 5 g 5-chloro-N-cyano-2,1,3-benzothiadiazol-4-amine are added to a solution of 0.55 g sodium in 60 ml ethanol and the mixture is reacted with 3 g allyl bromide. The mixture is agitated 3 hours under refluxing and the solvent evaporated under vacuum. The residue is extracted with methylene chloride. N-allyl-5-chloro-N-cyano-2,1,3-benzothiadiazol-4-amine (M.P. 62°–63°) is obtained.

The following compounds of formula I may be obtained in an analogous manner by appropriate substitution of a corresponding compound of formula II wherein B' is >NH (process variant a) or by reaction of a corresponding compound of formula III wherein Q is cyano with a corresponding ethylene or propylene diamine (process variant b):

| Example No. | Analogous to Ex. No. | A | B | C | M.P. |
|---|---|---|---|---|---|
| (I) N—C—bond | | | | | |
| 5 | 1 and 4 | 5-chloro-2,1,3-benzothiadiazol-4-yl |  N—Me | 4,5-dihydro-1H—imidazol-2-yl | b 128–131° |
| 6 | 1 and 4 | 5-chloro-2,1,3-benzothiadiazol-4-yl |  N—Me | 4,5-dihydro-1H—1-methylimidazol-2-yl | b 165–185° |
| 7 | 1 and 4 | 5-chloro-2,1,3-benzothiadiazol-4-yl |  N—Et | 4,5-dihydro-1H—imidazol-2-yl | b 132–135° |
| 8 | 1 and 4 | 5-chloro-2,1,3-benzothiadiazol-4-yl |  N—Bz | 4,5-dihydro-1H—imidazol-2-yl | b 132–134° |

-continued

| Example No. | Analogous to Ex. No. | A | B | C | M.P. |
|---|---|---|---|---|---|
| 9 | 1 and 4 | 5-chloro-2,1,3-benzothiadiazol-4-yl | ⟩N—crotyl | 4,5-dihydro-1H—imidazol-2-yl | b 151–154° |
| 10 | 1 and 4 | 5-chloro-2,1,3-benzothiadiazol-4-yl | ⟩N—CH$_2$C(Me)=CH$_2$ | 4,5-dihydro-1H—imidazol-2-yl | b 131–134° |
| 11 | 1 and 4 | 5-chloro-2,1,3-benzothiadiazol-4-yl | ⟩N—CH$_2$C(Cl)=CH$_2$ | 4,5-dihydro-1H—imidazol-2-yl | b 139–141.5° |
| 12 | 1 and 4 | 5-chloro-2,1,3-benzothiadiazol-4-yl | ⟩N—CH$_2$CH=CMe$_2$ | 4,5-dihydro-1H—imidazol-2-yl | b 112–114° |
| 13 | 1 and 4 | 5-chloro-2,1,3-benzothiadiazol-4-yl | ⟩N—CH$_2$CH=CH—Phe | 4,5-dihydro-1H—imidazol-2-yl | b 136–140° |
| 14 | 1 and 4 | 5-chloro-2,1,3-benzothiadiazol-4-yl | ⟩N—iPr | 4,5-dihydro-1H—imidazol-2-yl | b 138–141° |
| 15 | 1 and 4 | 5-chloro-2,1,3-benzothiadiazol-4-yl | ⟩N—iBu | 4,5-dihydro-1H—imidazol-2-yl | b 154° |
| 16 | 1 and 4 | 5-chloro-7-methyl-2,1,3-benzothiadiazol-4-yl | ⟩N—allyl | 4,5-dihydro-1H—imidazol-2-yl | b 153–157° |
| 17 | 1 and 4 | 4-methyl-2,1,3-benzothiadiazol-5-yl | ⟩N—allyl | 4,5-dihydro-1H—imidazol-2-yl | b 122–124° |
| 18 | 1 and 4 | 5-chloro-2,1,3-benzothiadiazol-4-yl | ⟩N—allyl | 4,5-dihydro-1H—1-methylimidazol-2-yl | b 108–110° |
| 19 | 1 and 4 | 5-chloro-2,1,3-benzothiadiazol-4-yl | ⟩N—CH$_2$—cyclopropyl | 4,5-dihydro-1H—imidazol-2-yl | b 165–167° |
| 20 | 1 and 4 | 4-bromo-2,1,3-benzothiadiazol-5-yl | ⟩N—allyl | 4,5-dihydro-1H—imidazol-2-yl | b 143–147° |
| 21 | 1 and 4 | 7-chloro-5-methyl-2,1,3-benzothiadiazol-4-yl | ⟩N—allyl | 4,5-dihydro-1H—imidazol-2-yl | b 162–165° |
| 22 | 1 and 4 | 5-methyl-2,1,3-benzothiadiazol-4-yl | ⟩N—allyl | 4,5-dihydro-1H—imidazol-2-yl | b 127–130° |

-continued

| Example No. | Analogous to Ex. No. | A | B | C | M.P. |
|---|---|---|---|---|---|
| 23 | 1 and 4 | 5-methyl-2,1,3-benzothiadiazol-4-yl | \N—allyl / | 4,5-dihydro-1H—imidazol-2-yl | b 125–127° |
| 24 | 1 and 4 | 5,7-dimethyl-2,1,3-benzoxadiazol-4-yl | \N—allyl / | 4,5-dihydro-1H—imidazol-2-yl | b 161–164° |
| 25 | 1* and 4** | 5-chloro-2,1,3-benzothiadiazol-4-yl | \N—(CH₂)₃CO—⌬—F / | 4,5-dihydro-1H—imidazol-2-yl | ta 201–203° |
| 26 | 1 and 4 | 5-chloro-2,1,3-benzothiadiazol-4-yl | \N—CH₂CH₂—O—Phe / | 4,5-dihydro-1H—imidazol-2-yl | hfu 175–178° |
| 27 | 1 and 4 | 5-chloro-2,1,3-benzothiadiazol-4-yl | \N—CH₂CH₂—O—⌬—OH / | 4,5-dihydro-1H—imidazol-2-yl | fu 276–278° |
| 28 | 1 and 4 | 5-chloro-2,1,3-benzothiadiazol-4-yl | \N—CH₂CH₂—OCH₂—⌬—OMe / | 4,5-dihydro-1H—imidazol-2-yl | hfu 161–163° |
| 29 | 1 and 4 | 5-chloro-2,1,3-benzothiadiazol-4-yl | \N—CH₂CH₂—Phe / | 4,5-dihydro-1H—imidazol-2-yl | hfu 217–218° |
| 30 | 1 and 4 | 5-chloro-2,1,3-benzothiadiazol-4-yl | \N—CH₂CH₂—⌬—Me / | 4,5-dihydro-1H—imidazol-2-yl | br 262–264° |
| 31 | 1 and 4 | 5-chloro-2,1,3-benzothiadiazol-4-yl | \N—CH₂CH₂—⌬—OH / | 4,5-dihydro-1H—imidazol-2-yl | hfu 221–223° |
| 32 | 1 and 4 | 5-chloro-2,1,3-benzothiadiazol-4-yl | \N—CH₂CH₂—N⟨ ⟩O / | 4,5-dihydro-1H—imidazol-2-yl | fu 185–187° |
| 33 | 1 and 4 | 5-chloro-2,1,3-benzothiadiazol-4-yl | \N—CH₂C≡CH / | 4,5-dihydro-1H—imidazol-2-yl | hfu 210–211° |
| 34 | 1 and 4 | 5-chloro-2,1,3-benzothiadiazol-4-yl | \N—CH₂CH₂—N(Me,Me)(Me,Me) / | 4,5-dihydro-1H—imidazol-2-yl | fu 255–257° |
| (II) N—O—bond | | | | | |
| 35 | 2 + 3 | 5-chloro-2,1,3-benzothiadiazol-4-yl | \N—O—allyl / | 4,5-dihydro-1H—imidazol-2-yl | b 136–138° |

-continued

| Example No. | Analogous to Ex. No. | A | B | C | M.P. |
|---|---|---|---|---|---|
| 36 | 2 + 3 | 5-chloro-2,1,3-benzothiadiazol-4-yl | >N—O—Me | 4,5-dihydro-1H—imidazol-2-yl | b 127–129° |
| 37 | 2 + 3 | 5-chloro-2,1,3-benzothiadiazol-4-yl | >N—O—CH$_2$—◁ | 4,5-dihydro-1H—imidazol-2-yl | b 118–120° |
| 38 | 2 + 3 | 5-chloro-2,1,3-benzothiadiazol-4-yl | >N—O—CH$_2$C≡CH | 4,5-dihydro-1H—imidazol-2-yl | ch 183° (dec.) |
| 39 | 2 + 3 | 5-chloro-2,1,3-benzothiadiazol-4-yl | >N—O—CH$_2$C(Me)=CH$_2$ | 4,5-dihydro-1H—imidazol-2-yl | hfu 146–147° |
| 40 | 2 + 3 | 5-chloro-2,1,3-benzothiadiazol-4-yl | >N—O—CH$_2$CH=CHCH$_3$ | 4,5-dihydro-1H—imidazol-2-yl | hfu 155–156° |
| 41 | 2 + 3 | 5-chloro-2,1,3-benzothiadiazol-4-yl | >N—O—CH$_2$CH=CH—Phe | 4,5-dihydro-1H—imidazol-2-yl | hfu 178–179° |
| 42 | 2 + 3 | 5-chloro-2,1,3-benzothiadiazol-4-yl | >N—O—CH$_2$CH$_2$OH | 4,5-dihydro-1H—imidazol-2-yl | hfu 144–146° |

*The substitution reaction of 5-chloro-N—(4,5-dihydro-1H—imidazol-2-yl)-2,1,3-benzothiadiazol-4-amine may also be effected with 4-chloro-p-fluorobutyrophenone in protected form, i.e. wherein the keto moiety is protected in the form of a 1,3-dioxolane-2-yl moiety and the resultant compound may thereafter be deprotected using dilute aqueous hydrochloric acid solution
**The cyclization reaction may also be effected with the starting compound having the keto moiety in the p-fluorobutyrophenone group protected in the form of a 1,3-dioxolane-2-yl moiety and the resultant compound may thereafter be deprotected using dilute aqueous hydrochloric acid solution.
M.P. = melting point
dec. = decomposition
b = in free base form
br = in hydrobromide acid addition salt form
ch = in hydrochloride acid addition salt form
fu = in fumarate acid addition salt form
hfu = in hydrogen fumarate acid addition salt form
ta = in acid addition salt form as tartrate
iBu = isobutyl  Bz = benzyl  Et = ethyl
Me = methyl  Phe = phenyl  iPr = isopropyl The following compounds of formula I may also be obtained in analogous manner:

| Example | A | B | C |
|---|---|---|---|
| (I) N—C—bond | | | |
| a | 2,1,3-benzothiadiazol-5-yl | >N—CH$_2$CH$_2$C(CH$_3$)$_2$CH$_2$OH | 3,4,5,6-tetrahydro-3-tert-butylprimidin-2-yl |
| b | 7-bromo-6-cyano-2,1,3-benzoxadiazol-4-yl | >N—◁ | 3,4,5,6-tetrahydro-3-ethyl-pyrimidin-2-yl |
| c | 4-ethyl-7-ethoxy-6-ethylthio-2,1,3-benzothiadiazol-5-yl | >N—(CH$_2$)$_2$—(2,2,5,5-tetraethyl-pyrrolidin-1-yl) | 3,4,5,6-tetrahydro-3-isopropyl-pyrimidin-2-yl |

-continued

| Example | A | B | C |
|---|---|---|---|
| d | 5-cyano-7-hydroxy-2,1,3-benzoxadiazol-4-yl | 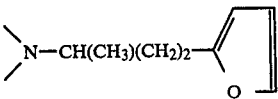 >N—CH(CH₃)(CH₂)₂—(furan) | 4,5-dihydro-1H—imidazol-2-yl |
| e | 7-cyano-2,1,3-benzoxadiazol-4-yl | 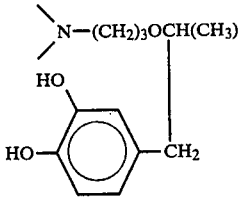 >N—(CH₂)₃OCH(CH₃)—(3,4-dihydroxyphenyl)CH₂ | 4,5-dihydro-1H—imidazol-2-yl |
| (II) N—O—bond | | | |
| f | 2,1,3-benzothiadiazol-5-yl | >N—O—CH₂CH(OH)CH₂CH₂CH₃ | 3,4,5,6-tetrahydro-3-tert-butylpyrimidin-2-yl |
| g | 5-fluoro-6-isopropoxy-2,1,3-benzoxadiazol-4-yl |  >N—O—cycloheptyl | 3,4,5,6-tetrahydro-3-ethyl-pyrimidin-2-yl |
| h | 4-cyano-2,1,3-benzothiadiazol-5-yl | 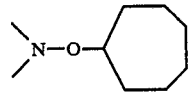 >N—O—(CH₂)₂CH(CH₃)—cyclopentyl | 4,5-dihydro-1H—1-isopropyl-imidazol-2-yl |
| i | 6-isopropylthio-2,1,3-benzoxadiazol-5-yl | >N—O—(CH₂)₃—(2,2,6,6-tetraisopropylpiperidin-1-yl) | 4,5-dihydro-1H—1-methyl-imidazol-2-yl |
| j | 7-hydroxy-2,1,3-benzothiadiazol-4-yl | 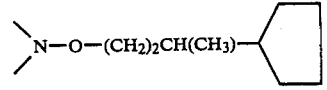 >N—O—(CH₂)₄—pyridyl | 3,4,5,6-tetrahydro-3-methylpyrimidin-2-yl |
| k | 6-isopropyl-2,1,3-benzoxadiazol-5-yl | >N—OH | 4,5-dihydro-1H—1-ethyl-imidazol-2-yl |
| l | 7-methylthio-2,1,3-benzoxadiazol-5-yl | 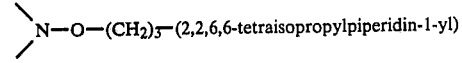 >N—O—CH₂C≡CCH₂—(aryl-OCH₂CH₃, CH₂CH₃) | 4,5-dihydro-1H—imidazol-2-yl |

In a 1st group of compounds n is 2.
In a 2nd group of compounds n is 3.
In a 3rd group of compounds X is oxygen.
In a 4th group of compounds X is sulfur.
In a 5th group of compounds Y is a bond.
In a 6th group of compounds Y is oxygen.
In a 7th group of compounds $R_1$, $R_2$ and $R_3$ independently are hydrogen, halogen, alkyl or alkoxy.
In an 8th group of compounds $R_4$ has significance (i) mentioned above.
In a 9th group of compounds $R_4$ has significance (ii) mentioned above.
In a 10th group of compounds $R_4$ has significance (iii) mentioned above.
In a 11th group of compounds $R_4$ has significance (iv) mentioned above.
In a 12th group of compounds $R_5$ is hydrogen.
In a 13th group of compounds $R_5$ is alkyl.

The compounds of the invention are useful because they exhibit pharmacological activity in animals.

The compounds possess bradycardiac activity, as indicated by standard tests. For example, in the spontaneously-beating right ventricle of the guinea pig (method of Dixon, A.K. et al., *Arzneim.F.* 27 [1977] 1968–1979) a decrease in the heart rate is observed at a bath concentration of from about 1 μM to about 100 μM.

Thus, the following activity is observed in the above mentioned test for the compound of Example 1 and the standard AQ-A 39, i.e. 5,6-dimethoxy-2-{3-N-[2-(3,4-dimethoxyphenyl)ethyl]-(N-methyl)amino]propyl}phthalimidine:

| Compound | EC$_{25}$ ($\mu$M) |
|---|---|
| Example 1 | 3.0 |
| AQ-A 39 | 3.4 |

In the pithed rat preparation (method of H. Kleinlogel et al., Europ.J.Pharmacol. 33 [1975] 159–163) the compounds exhibit heart rate decreasing activity at a dosage of about 0.3 to about 10 mg/kg i.v.

Thus, the following activity is observed in the above-mentioned test for the compound of Example 1 and the standard AQ-A 39:

| Compound | ED$_{25}$ (mg/kg i.v.) |
|---|---|
| Example 1 | 1.4 |
| AQ-A 39 | 4.6 |

The compounds are devoid of peripheral α-mimetic activity, as evidenced by the observation that the bradycardiac activity is not accompanied by any significant vasoconstriction or blood pressure increase.

The compounds of the invention may be administered in similar manner to known standards for use in the above-mentioned bradycardiac utility, for example AQ-A 39. The suitable daily dosage for a particular compound will depend on a number of factors such as its relative potency of activity. As indicated in the above-mentioned test results for the compound of Example 1, it is therefore indicated that this compound may be administered at similar or lower dosage than conventionally to be employed for e.g. AQ-A 39.

The compounds of the invention are therefore useful as bradycardiac agents, e.g. for the prophylaxis and treatment of cardiac disorders such as Angina pectoris or heart rhythm disturbances such as sinus tachycardia.

Preferred in this indication are the compounds of Examples 1, 3, 10, 15, 19, 23, 28, 30 and 41, especially of Examples 1, 3 and 10, particularly of Example 1.

Additionally, some of the compounds, in particular those of formula Ia wherein Y is oxygen, exhibit a pronounced degree of membrane-stabilizing activity which may make them particularly useful in the treatment of heart rhythm disturbances not necessarily related to a sinus tachycardia.

For the above-mentioned use the dosage will, of course, vary depending on the compound employed, mode of administration and treatment desired. However, in general, satisfactory results are obtained when administered at a daily dosage of from about 0.07 mg to about 1.5 mg per kg animal body weight, conveniently given in divided doses 2 to 4 times a day or in sustained release form. For the larger mammals, the total daily dosage is in the range of from about 5 mg to about 100 mg, and dosage forms suitable for oral administration comprise from about 1.25 mg to about 50 mg of the compounds admixed with a solid or liquid pharmaceutical carrier or diluent. An example of a daily dosage is from about 10 to about 100 mg, preferably from about 10 mg to about 20 mg.

The compounds of the invention additionally exhibit anti-tremor activity, as indicated by standards tests. This appears e.g. from the following test with mice, wherein a tremor antagonism is observed on p.o. administration of from about 10 to about 100 mg/kg animal body weight of the compounds:

The evening before the test day the mice used for the test (50% males and 50% females) are deprived of feed. Groups of ten animals each are used for the test, one group forming the control group. The compound to be tested is administered to the animals in each group, the doses increasing from group to group. A physiological saline solution is given to the animals of the control group. 30 minutes after administration of the compound to be tested, 100 mg/kg animal body weight of a tremor-producing compound (2,6-dichlorophenyl-acetimidoyl ureide) is administered p.o. to all the animals. 5, 10, 15 and 20 minutes after administration of the tremor-producing compound the animals are judged in accordance with the following scale: 2=strong tremor; 1=weak tremor; 0=no tremor. Evaluation is then effected: for the three first measurements (5, 10 and 15 minutes after administration), the behaviour of each mouse is determined, and the group average values are estimated as follows:

group with strong tremor=averages 1.5–2.0 group with weak tremor=averages 0.5–1.5 group without tremor=averages 0–0.5

The compounds of the invention are therefore useful as anti-tremor agents.

The compounds also exhibit anti-rigor activity, as indicated by standard tests. This appears e.g. from the following test with rats, wherein a rigor antagonism is observed on i.v. administration of from about 0.001 to about 10 mg/kg animal body weight of the compounds:

Rats are injected i.p. with 7.5 mg/kg animal body weight of Thalamonal (Registered Trade Mark), whereupon these animals develop a rigor which can be measured with an electromyograph. The dose of active compound which must be injected i.v. in order to inhibit the rigor of the rats is then ascertained.

The compounds are therefore further useful as anti-rigor agents.

The compounds of the invention also exhibit myotonolytic activity, as indicated by standard tests. For example, in rabbits on i.v. administration of from 0.001 to 0.1 mg/kg animal body weight of the compounds a significant muscle relaxing effect is observed in accordance with the method of Teschendof et al., Arch. Exp. Pharmacol. 266, 467–468 (1970).

The compounds are therefore further useful as myotonolytics, for example for the treatment of spastic conditions of different etiology (neurological, inflammatory, rheumatic, etc.) and muscle relaxants.

The compounds also exhibit tranquillizing and sedating acitivity, as indicated by standard tests. Thus, the compounds suppress motility as can be demonstrated in mice. In one test two groups, each comprising four mice (one group as a control group), administered with 0.01 mg/kg to 1.0 mg/kg p.o. of the test compound is placed in a cage in redlight (Electronic Motility Testing obtainable from Motron-Producter, Stockholm, Sweden). The number of times the mice interrupt the light beams is counted electronically every fifteen minutes over a period of 60 minutes. Furthermore, the compounds reduce defensive ambivalence behaviour (a form of conflict behaviour) and increase social contact in standard animal introduction tests. In one test a male mouse administered with 0.1 to 1 mg/kg p.o. of the compound is placed for 6 minutes into the home cage of an isolated, aggressive male mouse. The behaviour of the introduced mouse is then statistically analysed according to the method of A. K. Dixon and J. H. Mackintosh, *Anim. Behav.* 19, 138–140 (1971) using the behavioural categories outlined by A. K. Dixon "Rodent Social Behaviour in Relation to Biomedical Research" in "Das Tier im Experiment", Ed. W. Weihe, Hans Huber Verlag, Bern 1978, e.g. nonsocial activity, social investigation and mating, aggression, defensive ambivalence, fleeing or retreating and feeding behaviour. Furthermore, on administration of 0.3 to 3 mg/kg p.o. of the compounds to rats in the sleep/wake cycle carried out in accordance with the principles of H. Kleinlogel et al., *European J. Pharmacol.* 33, 159–163 (1975) an increase of dozing is observed. The EEG is recorded over 8 hours.

The compounds are therefore useful as tranquillizers and sedatives.

The compounds also exhibit antidepressive activity, as indicated by standard tests. Thus, an inhibition of tetrabenazine-induced catalepsy and ptosis in rats is observed upon intraperitoneal administration of from 5 to 20 mg/kg animal body weight of the compounds in accordance with the method described by Stille (*Arznei-mittel-Forsch.* [1964] 14, 534). Furthermore, the compounds on admininstration of from 1 to 30 mg/kg i.p. to mice reduce the immobility induced by water-immersion according to the method desdribed by R. D. Porsolt et al., *Arch.Int.Pharmacodyn.* 229, 327–336 (1977).

The compounds are therefore useful as antidepressants, e.g. for the treatment of somatogenic, endogenous and psychogenous depressions.

For the above-mentioned uses as anti-tremor, anti-rigor, myotonolytic, and muscle relaxant, tranquillizing and sedative, and antidepressant agents the dosage will, of course, vary depending on the compound employed, mode of administration and therapy desired. However, in general, satisfactory results are obtained with a daily dosage of from about 0.01 mg to about 10 mg per kg animal body weight, conveniently given in divided doses 2 to 4 times a day or in sustained release form. For the larger mammal, the total daily dosage is in the range from about 0.2 mg to about 200 mg. The dose is conveniently administered in divided doses 2 to 4 times a day in unit dosage form containing from about 0.05 mg to about 100 mg of the compound admixed with a solid or liquid pharmaceutical carrier or diluent.

It is to be appreciated that a compound may have to be administered for at least 4 weeks before a significant anti-depressant effect is observed.

The compounds may be administered in free form or in pharmaceutically acceptable salt form, preferably acid addition salt form. Such salt forms exhibit the same order of activity as the free forms and are readily prepared in conventional manner. The present invention also provides a pharmaceutical composition comprising a compound of the invention in free form or in pharmaceutically acceptable salt form, in association with a pharmaceutical carrier or diluent. Such compositions may be in the form of, for example, a solution or a tablet.

We claim:

4. The compound of claim 1 which is N-allyl-5-chloro-N-(4,5-dihydro-1H-imidazol-2-yl)-2,1,3-benzothiadiazol-4-amine or a pharmaceutically acceptable salt form thereof.

2. A method of treating bradycardia which comprises administering to an animal in need of such treatment a therapeutically effective amount of a compound of claim 1.

3. A pharmaceutical composition useful in treating bradycardia comprising a pharmaceutically acceptable carrier or diluent and a therapeutically effective amount of a compound of claim 1, or a pharmaceutically acceptable salt form thereof.

1. A compound of the formula

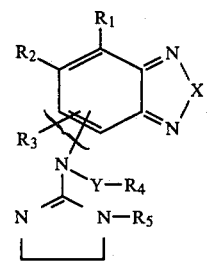

wherein
X is oxygen or sulfur;
Y is a bond or oxygen;
$R_1$, $R_2$ and $R_3$, independently, are hydrogen, chloro, bromo, alkyl of 1 or 2 carbon atoms or alkoxy of 1 or 2 carbon atoms;
$R_4$ is alkyl of 1 to 6 carbon atoms optionally monosubstituted by hydroxy or halo of atomic number of from 9 to 53 and wherein the hydroxy or halo moiety is separated from Y by at least 2 carbon atoms; alkenyl of 3 to 6 carbon atoms optionally monosubstituted by halo of atomic number of from 9 to 53 and wherein the double bond and the halo moiety are separated from Y by at least 2 carbon atoms; alkynyl of 3 to 6 carbon atoms wherein the triple bond is separated from Y by at least 2 carbon atoms; cycloalkyl of 3 or 5 carbon atoms; or cycloalkylalkyl of 3 or 5 carbon atoms in the cycloalkyl moiety and of 1 to 4 carbon atoms in the alkyl moiety thereof;
and $R_5$ is hydrogen or alkyl of 1 to 4 carbon atoms;
or a pharmaceutically acceptable salt form thereof.

5. A compound of claim 1 having the formula

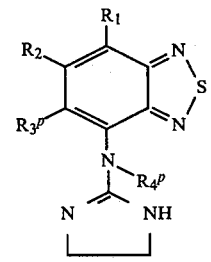

wherein
$R_1$ and $R_2$ are as defined in claim 1; $R_3^P$ has the same significance as $R_3$ in claim 1;
and $R_R^P$ is alkyl of 1 to 6 carbon atoms; alkenyl of 3 to 6 carbon atoms wherein the double bond is separated from the nitrogen atom by at least 2 carbon atoms; 2-chloro-2-propenyl; alkynyl of 3 to 6 carbon atoms wherein the triple bond is separated from the nitrogen atom by at least 2 carbon atoms;

cycloalkyl of 3 or 5 carbon atoms; or cycloalkylalkyl of 3 or 5 carbon atoms in the cycloalkyl moiety and of 1 to 4 carbon atoms in the alkyl moiety thereof, the total number of carbon atoms not exceeding 7;

or a pharmaceutically acceptable salt form thereof.

6. A compound of claim 1 having the formula

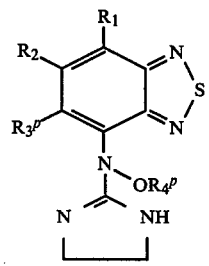

wherein
$R_1$ and $R_2$ are as defined in claim 1; $R_3{}^P$ has the same significance as $R_3$ in claim 1;
and $R_4{}^P$ is alkyl of 1 to 6 carbon atoms; alkenyl of 3 to 6 carbon atoms wherein the double bond is separated from the nitrogen atom by at least 2 carbon atoms; 2-chloro-2-propenyl; alkynyl of 3 to 6 carbon atoms wherein the triple bond is separated from the nitrogen atom by at least 2 carbon atoms; cycloalkyl of 3 or 5 carbon atoms; or cycloalkylalkyl of 3 or 5 carbon atoms in the cycloalkyl moiety and of 1 to 4 carbon atoms in the alkyl moiety thereof, the total number of carbon atoms not exceeding 7;
or a pharmaceutically acceptable salt form thereof.

* * * * *